(12) United States Patent
Myllykangas et al.

(10) Patent No.: US 11,322,900 B2
(45) Date of Patent: May 3, 2022

(54) POLYMER HOLDER, ELECTRODE SYSTEM AND MANUFACTURING AND HANDLING METHODS OF POLYMER HOLDER

(71) Applicant: Bittium Biosignals Oy, Kuopio (FI)

(72) Inventors: Juha Myllykangas, Kuopio (FI); Arto Nikula, Lumijoki (FI); Arto Remes, Kuopio (FI)

(73) Assignee: Bittium Biosignals Oy, Kuopio (FI)

( * ) Notice: Subject to any disclaimer, the term of this patent is extended or adjusted under 35 U.S.C. 154(b) by 757 days.

(21) Appl. No.: 16/191,170

(22) Filed: Nov. 14, 2018

(65) Prior Publication Data

US 2019/0334304 A1    Oct. 31, 2019

Related U.S. Application Data

(63) Continuation-in-part of application No. 15/966,785, filed on Apr. 30, 2018, now Pat. No. 11,229,390.

(51) Int. Cl.
*H01R 33/97* (2006.01)
*A61B 5/00* (2006.01)
(Continued)

(52) U.S. Cl.
CPC ........... *H01R 33/97* (2013.01); *A61B 5/6833* (2013.01); *A61B 5/6835* (2013.01); *A61B 5/291* (2021.01); *A61B 5/296* (2021.01); *A61B 2562/16* (2013.01)

(58) Field of Classification Search
CPC ........ A61B 2562/221; A61B 2562/222; A61B 2562/225; A61B 2562/226; A61B 5/25;
(Continued)

(56) References Cited

U.S. PATENT DOCUMENTS 6,398,579 B1 * 6/2002 Banas ............... H01R 13/6273
439/350
9,277,864 B2 * 3/2016 Yang ....................... A61B 5/05
(Continued)

FOREIGN PATENT DOCUMENTS

EP    1 559 335 A2    8/2005
EP    2 468 181 A1    6/2012
(Continued)

OTHER PUBLICATIONS

Extended European Search Report received for European Patent Application Serial No. 19168010.7 dated Sep. 3, 2019, 9 pages.

*Primary Examiner* — Eun Hwa Kim
(74) *Attorney, Agent, or Firm* — FisherBroyles, LLP (57) ABSTRACT

A polymer holder for a biosignal processing device, wherein a wall of the polymer holder forms a pocket, and the wall follows an outer contour of the biosignal processing device. The polymer holder has a first aperture for inserting the biosignal processing device into the pocket and removing the biosignal processing device from the pocket. The polymer holder includes an electrically conductive contact structure, which is in a wired electric contact with electrodes that receive the at least one biosignal, at a rear section opposite to the first aperture, and the electrically conductive contact structure is at least partly attached inside the wall. The electrically conductive contact structure is electrically connected with a counterpart of the biosignal processing device in response to an insert of the biosignal processing device in the pocket.

12 Claims, 6 Drawing Sheets

(51) Int. Cl.
*A61B 5/296* (2021.01)
*A61B 5/291* (2021.01)

(58) Field of Classification Search
CPC ....... A61B 5/271; A61B 5/273; A61B 5/6802;
A61B 5/6803; A61B 5/6804; A61B
5/6805; A61B 5/6813; A61B 5/6823;
A61B 5/6838; H01R 33/97
See application file for complete search history.

(56) References Cited

U.S. PATENT DOCUMENTS

| | | | |
|---|---|---|---|
| 2012/0035426 A1* | 2/2012 | Mielcarz | A61B 5/0015 |
| | | | 600/300 |
| 2017/0026644 A1 | 1/2017 | Lee et al. | |
| 2018/0295895 A1* | 10/2018 | Donohoe | A61B 5/6807 |
| 2019/0350475 A1* | 11/2019 | Dietz | A61B 5/0532 |

FOREIGN PATENT DOCUMENTS

| | | |
|---|---|---|
| WO | 2014033360 A1 | 3/2014 |
| WO | 2014/057083 A2 | 4/2014 |
| WO | 2015/127218 A1 | 8/2015 |
| WO | 2015/189476 A1 | 12/2015 |

\* cited by examiner

POLYMER HOLDER, ELECTRODE SYSTEM AND MANUFACTURING AND HANDLING METHODS OF POLYMER HOLDER

CROSS-REFERENCE TO RELATED APPLICATION

This application is a continuation-in-part application of U.S. patent application Ser. No. 15/966,785, filed Apr. 30, 2018, which is incorporated by reference herein in its entirety.

BACKGROUND

Field

The invention relates to a polymer holder, an electrode system and manufacturing and handling methods of the polymer holder.

Description of the Related Art

An electronic device, which measures biosignals such as ECG (ElectroCardioGram) and EEG (ElectroEncephalo-Gram), must be well contacted with the electrodes that are in contact with the body and mechanically reliably fixed to its support. The electronic device should also be easily removable from the support. A good attachment with easy detachment has not yet been discovered. Hence, there is a need for improvement.

SUMMARY

The invention is defined by the independent claims. Embodiments are defined in the dependent claims.

BRIEF DESCRIPTION OF THE DRAWINGS

Example embodiments of the present invention are described below, by way of example only, with reference to the accompanying drawings, in which.

DETAILED DESCRIPTION

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some features are irrelevant to the actual invention. Therefore, they need not be discussed in more detail here.

Figure 1A:
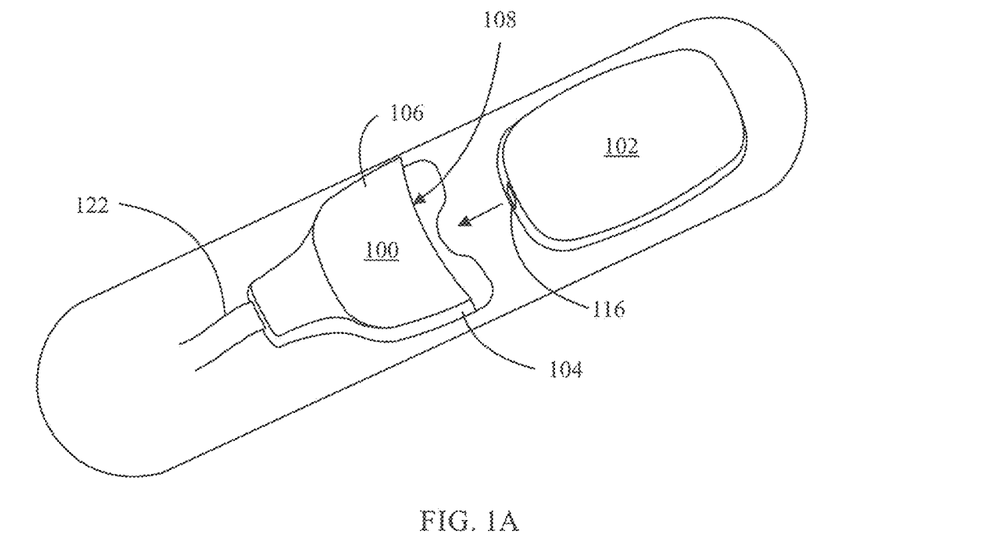
FIGS. 1A and 1B illustrate examples of polymer holders.
Figure 1B:
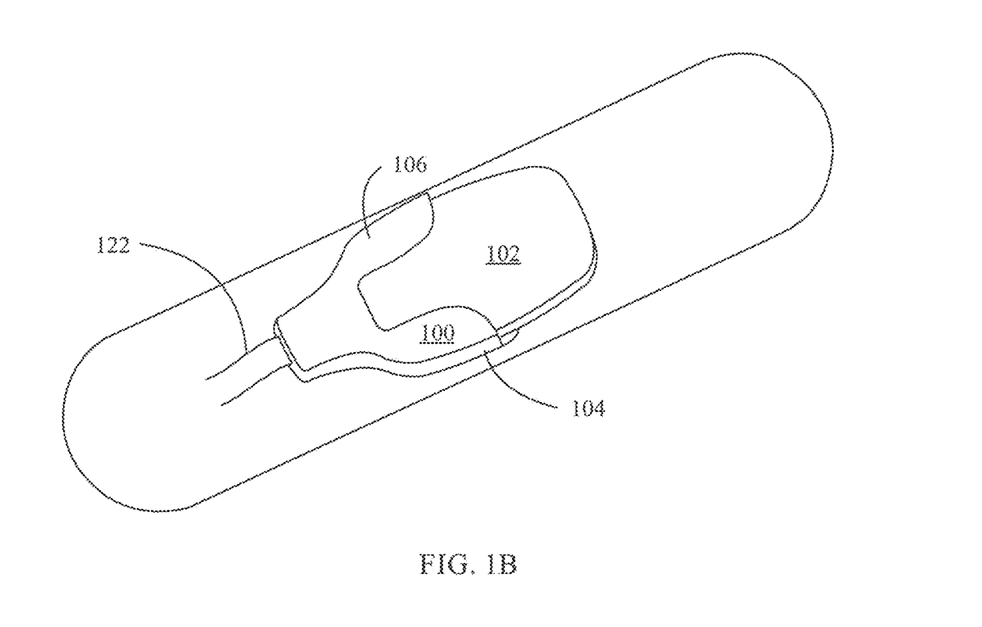

FIGS. 1A and 1B illustrate example of polymer holders 100 for a biosignal processing device 102. In FIG. 1B, the polymer holder 100 has a slit in the front part whereas the polymer holder 100 of FIG. 1A does not have it. The name refers to the fact that the polymer holder 100 is made of polymer such as plastic. The biosignal processing device 102 may be an electronic device which may convert an analog biosignal it receives to a digital biosignal. The biosignal processing device 102 may also filter the biosignal in the analog or in the digital form. Additionally or alternatively, the biosignal processing device 102 may perform data processing of the biosignal, and it may also store data of the biosignal and/or a result of its processing. The biosignal may be related to body movement, body temperature, heart rate variability, electrocardiogram, electromyogram, electroencephalogram or the like for example.

In FIG. 1A the biosignal processing device 102 is outside the polymer holder 100. The arrow in FIG. 1A illustrates the feature that the biosignal processing device 102 can be inserted in the polymer holder 100. In FIG. 1B the biosignal processing device 102 is inserted in the polymer holder 100.

A wall 104 of the polymer holder 100 forms a pocket 106, and the wall 104 follows an outer contour of the biosignal processing device 102. The pocket 106 is a free space or volume into which a part of the biosignal processing device 102 fits accurately. A degree of precision with which the surfaces of the biosignal processing device 102 and the polymer holder 100 are adapted to each other may be high enough to enable operation with one hand or without seeing the actual movement of processing device 102. A friction between an outer surface of the biosignal processing device 102 and an inner surface of the polymer holder 100 may keep the biosignal processing device 102 in the polymer holder 100 even under accelerations caused by sport activities or in upside down positions. The fit between the biosignal processing device 102 and the polymer holder 100 may be rather tight resulting in a suitable friction and suction force. Polymer material of the holder 100 is also slightly flexible and even stretchable which enables to achieve a suitable tightness and friction and suction force between the polymer holder 100 and the biosignal processing device 102. The pocket 106 has the wall 104 round the biosignal processing device 102 in a continuous hemispherical manner, which is more secure and efficient than a wall that has a shape of band round the biosignal processing device 102, for example. Still, the hemispherical wall 104 allows easy removal of the biosignal processing device 102.

The polymer holder 100 has a first aperture 108 for inserting the biosignal processing device 102 into the pocket 106 and removing the biosignal processing device 102 from the pocket 106. The size of the aperture 108 may vary but a size and a shape of a cross section of the aperture 108 and the biosignal processing device 102 are about the same.

However in an embodiment, the aperture first 108 may be larger because there may be a clearance between the biosignal processing device 102 and the polymer holder 100, the clearance allowing a free play between the biosignal processing device 102 and the polymer holder 100 at the first aperture 108. In an embodiment, the clearance may be less than 1 mm. In an embodiment, the clearance may be less than 0.1 mm. In any embodiment, the clearance may be less than 0.01 mm. In any embodiment having the clearance, the clearance may be larger than 0.001 mm.

In an embodiment, the cross section of the first aperture 108 and/or the pocket 106 may be a slightly smaller than that of the biosignal processing device 102, because the polymer holder 100 may stretch. In this manner, the friction between the polymer holder 100 and the biosignal processing device 102 may be made stronger.

The polymer holder 100 includes an electrically conductive contact structure 110 at a rear section 114 of the polymer holder 100 opposite to the first aperture 108. The electrically conductive contact structure 110 may be in a wired electric contact with electrodes 112, which are configured to receive the at least one biosignal. The biosignal may be generated by a human or animal. The electrically conductive contact structure 110 may be at least partly attached to the wall 104, directly or indirectly to hold structure 100 in place. The electrically conductive contact structure 110 is configured to connect electrically with a counterpart 116 of the biosignal processing device 102 in response to an insert of the biosignal processing device 102 into the pocket 106. The electrically conductive contact structure 110 is also configured to connect mechanically with the counterpart 116 which may increase friction and thus permanence, immobility and/or stability of the biosignal processing device 102 partly within the polymer holder 100. By having a proper wall 104 around the biosignal processing device 102 in a form of the pocket 106 and a good electric contact inside the pocket 106 makes the biosignal processing device 102 to stay in the pocket 106 effectively even in rapid movements. The biosignal processing device 102 is also easy to take out from the pocket 106, because it is only partly therein.

Figure 2:
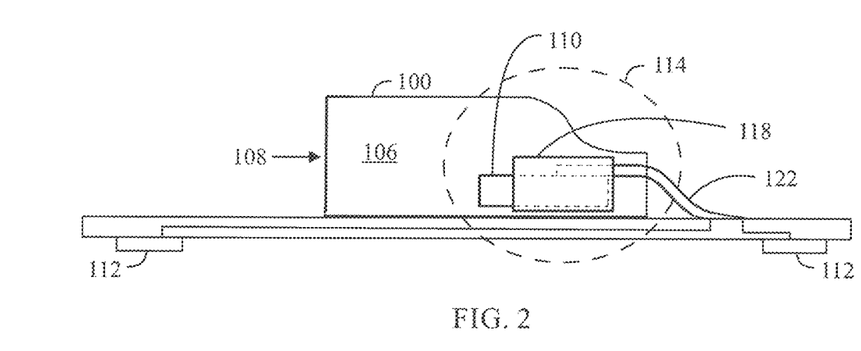
FIG. 2 illustrates an example of an electrically conductive contact structure within the polymer holder.

In an embodiment an example of which is illustrated in FIG. 2, the electrically conductive contact structure 110 may comprise a male connector that extends at least partly inside the pocket 106. The male connector may connect with a female connector of the biosignal processing device 102 in response to the insert of the biosignal processing device 102 in the pocket 106.

In an embodiment, the electrically conductive contact structure 110 may comprise a female connector, and the female connector is configured to connect with a male connector of the biosignal processing device 102 in response to the insert of the biosignal processing device 102 in the pocket 106.

In an embodiment, the male connector may be a male USB connector (USB=Universal Serial Bus), and the female connector may be a female USB connector. In an embodiment, the male connector may be a male micro USB connector, and the female connector may be a female micro USB connector.

In an embodiment, the electrically conductive contact structure 110 is partly within a cover 118 of an elastic material. In an embodiment, the cover 118 may be molded, and the electrically conductive contact structure 110 may be left within the elastic material. In an embodiment, the molding process may be injection molding.

Figure 3:
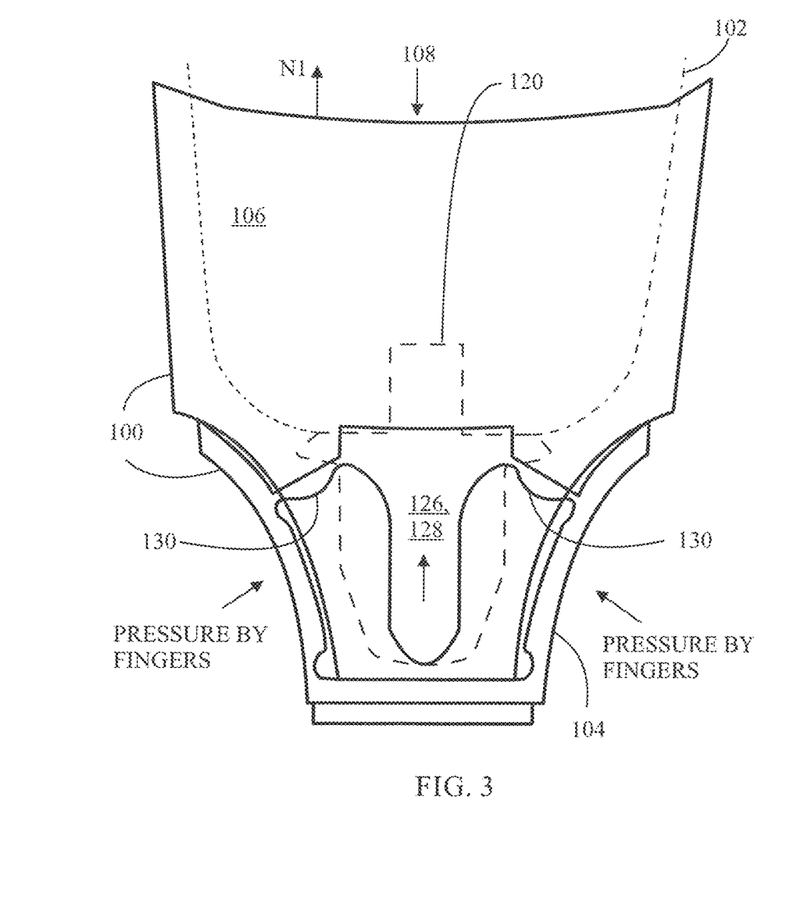
FIG. 3 illustrates an example of the polymer holder with a second aperture and a piston for moving a biosignal processing device fromward the polymer holder.
Figure 4:
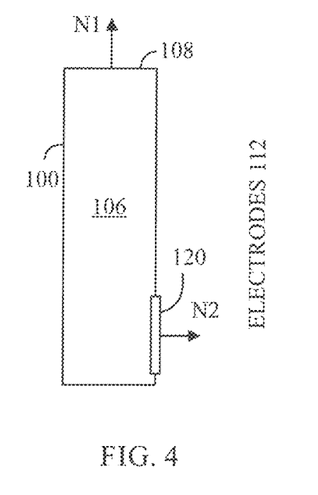
FIG. 4 illustrates an example of the polymer holder with the second aperture directed to a different direction from that of a first aperture.

In an embodiment an example of which is illustrated in FIG. 3, the polymer holder 100 may have a second aperture 120 at the rear section 114. A normal N2 of the second aperture 120 may be directed toward a direction perpendicular to a normal N1 of the first aperture 108, which is illustrated in FIG. 4. The second aperture 120 may be configured to open toward the electrodes 112, which is also illustrated in FIG. 4. The electrically conductive contact structure 110 may be inserted through the second aperture 120 into the polymer holder 100. The electrically conductive contact structure 110 may have the cover 118 while it is inserted through the second aperture 120. The electrically conductive contact structure 110 may be pig-tailed while inserting it through the second aperture 120 (see also FIGS. 1A, 1B and 2). A wire 122 of the pig-tail may connect the electrically conductive contact structure 110 with the electrodes 112.

Figure 5:
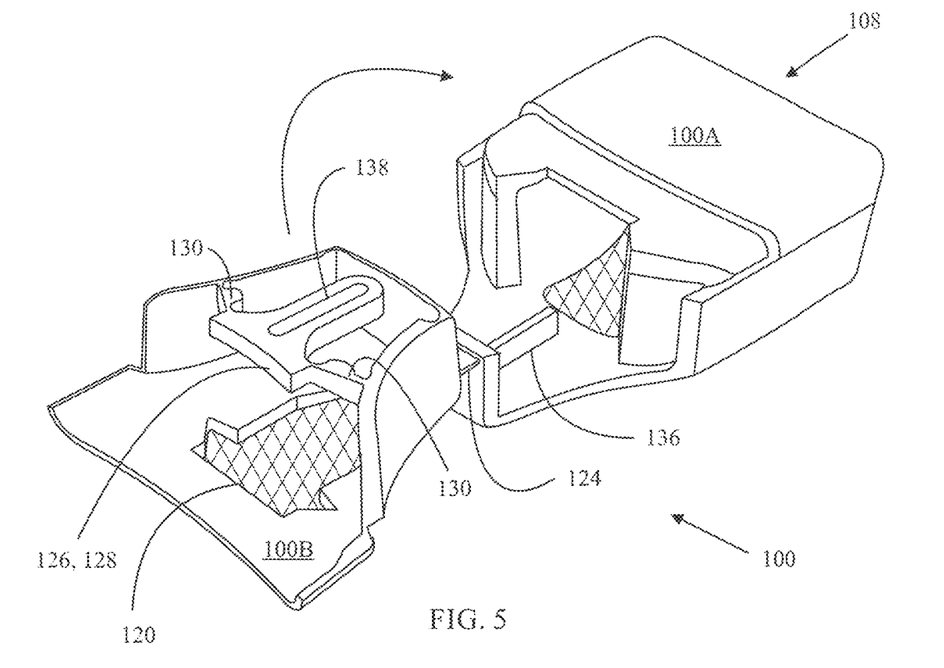
FIG. 5 illustrates an example of the polymer holder with a first part and a second part which are coupled with a hinge.

In an embodiment an example of which is illustrated in FIG. 5, the polymer holder 100 may comprise a first polymer part 100A, a second polymer part 100B and a flexible polymer hinge 124, which are of the same material combined together in a common molding process. The hatched parts in FIG. 5 are holes. In an embodiment, the molding process may be an injection molding process. The hinge 124 allows about 180° rotation between the first polymer part 100A and the second polymer part 100B such that the first polymer part 100A and the second polymer part 100B overlap each other for forming the usable polymer holder 100.

In an embodiment, the first polymer part 100A and the second polymer part 100B may be formed separately.

Figure 6:
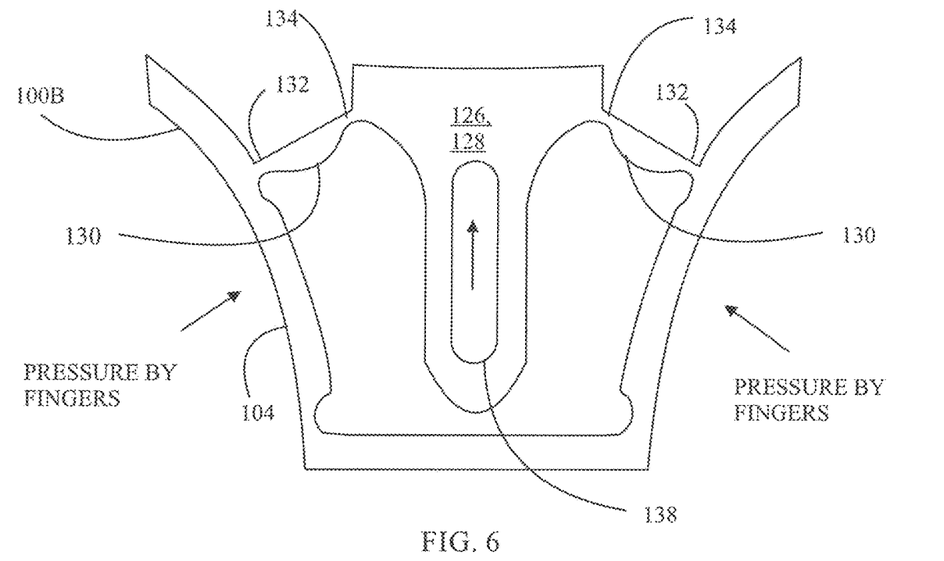
FIG. 6 illustrates an example of the second part with the hinged piston.

In an embodiment an example of which is illustrated in FIGS. 3, 5 and 6, the polymer holder 100 may comprise, at the rear section 114, a mechanism 126 which can cause a force to the biosignal processing device 102 directed toward the first aperture 108 in response to pressure against the polymer holder 100 at the rear section 114. The pressure against an outer surface of the polymer holder 100 may be caused by a user when he/she presses the polymer holder 100 by his/her fingers, for example. The force against and the movement of the biosignal processing device 102 with the help of the force provided by the mechanism 126 makes it easy to detach the biosignal processing device 102 from the pocket 106. The biosignal processing device 102 may be gripped with fingers from the upper part for lifting the biosignal processing device 102 and additionally the pressure against the polymer holder 100 results in a convenient removal of the biosignal processing device 102 from the pocket 106. In an embodiment, the mechanism 126 may move about 1 mm when a pressure is applied at the rear section 114. In an embodiment, the mechanism 126 may be configured to move about 2 mm when a pressure is applied at the rear section 114. The biosignal processing device 102 may be configured to move about the same length at the mechanism 126 when a pressure is applied at the rear section 114.

In an embodiment an example of which is shown in FIGS. 3, 5 and 6, the mechanism 126 may comprise a piston 128 that can move toward and fromwards the first aperture 108. The mechanism 126 may also comprise least one lever 130 hinged to the piston 128 at one end and to the polymer holder 100 at another end. A hinge 132 between the lever 130 and the polymer holder 100 may be made of the same material as the polymer holder 100. The hinge 134 between the lever 130 and the piston 128 may be made of the same material as the polymer holder 100. The common molding process enables this kind of hinging.

In an embodiment, the at least one lever 130 may be pushed forward and turn between the hinges 132, 134 in response to a pressure of the polymer holder 100 at the rear section 114. The lever 130 may turn between the hinges 132, 134. Then the lever 130 may move the piston 128 toward the first aperture 108 in response to the pressure. The piston 128 may then move the biosignal processing device 102 toward the first aperture 108.

In an embodiment an example of which is illustrated in FIG. 5, the polymer holder 100 (second part 100B) may have a rail 136 extending longitudinally in a direction from the rear section 114 to the first aperture 108. The piston 128 may have a slit 138 into which the rail 136 may be matched for guiding the movement of the piston 128 toward and fromward the first aperture 108.

In an embodiment, the wall 104 of the polymer holder 100 may droop in response to the pressure. The mechanism 126 may then redirect the force of the pressure to a force toward the first aperture 108 in order to move the biosignal processing device 102 thereto. As can be seen in FIG. 6 the wall 104 may easily bend at the hinges 132, 134.

Figure 7:
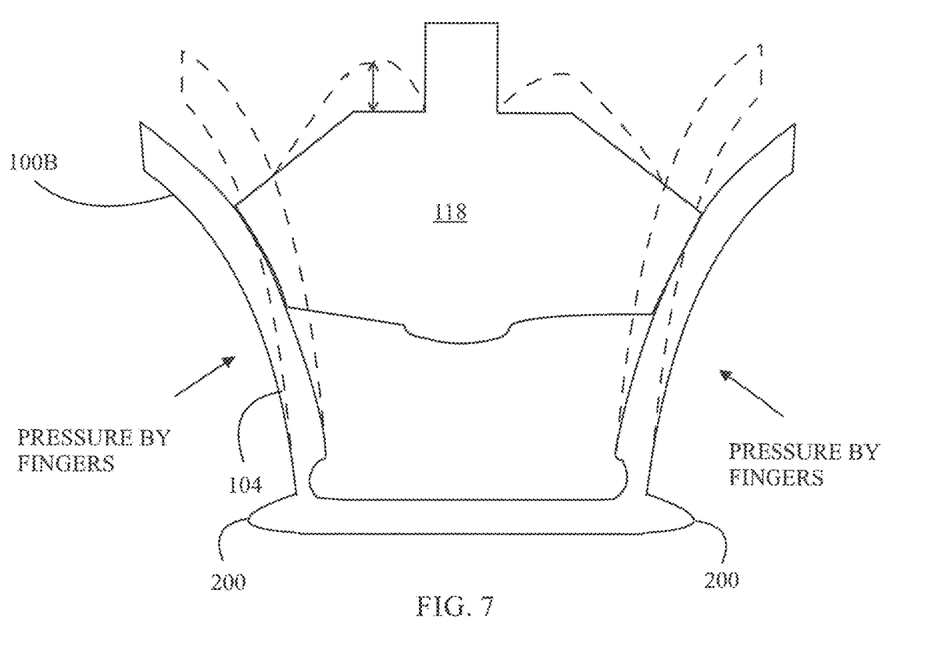
FIG. 7 illustrates an example of the second part with elastic material therein.

In an embodiment an example of which is shown in FIG. 7, the electrically conductive contact structure 110 may comprise elastic material as a cover 118 at the rear section 114. The pressure against the second part 100B of the polymer holder 100 may cause the elastic material of the cover 118 to reshape, push against and move the biosignal processing device 102 toward the first aperture 108 for enabling an easy removal. The dashed lines show the movement of the wall 104 of the second part 100B of the polymer holder 100 and the movement of elastic material of the cover 118 toward the first aperture 108. The elastic material of the cover 118 may revert to its original shape after the pressure ceases.

In an embodiment, the polymer holder 100 has extensions 200 at a farthest end from the first aperture 108 to ensure a good grip when the polymer holder 100 is squeezed.

Figure 8A:
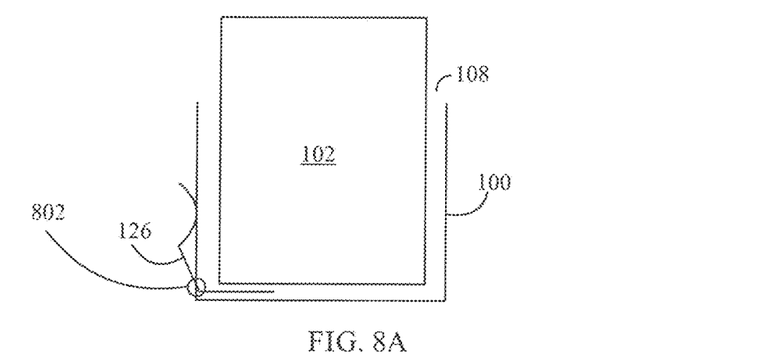
FIGS. 8A and 8B illustrate an example of a lever for pushing the biosignal processing device outward from the polymer holder.
Figure 8B:
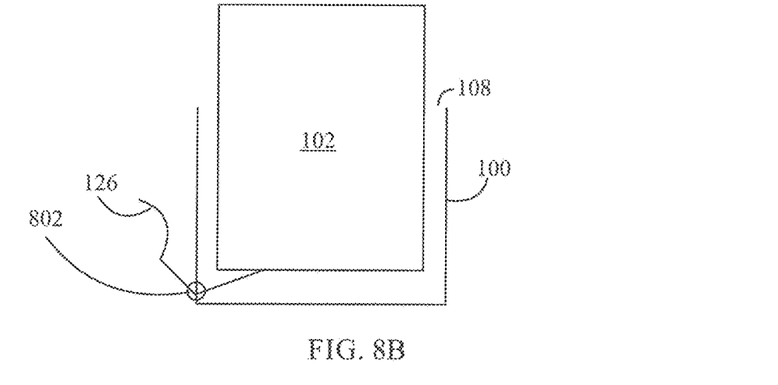

In an embodiment an example of which is shown in FIGS. 8A and 8B, the mechanism 126 may be a hand lifted lever 800 outside the polymer holder 100. The lever 800 may be hinged (hinge 802) at the wall 104 of the polymer holder 100. Then when the lever 800 is turned, an angled part of the lever 800 inside the polymer holder 100 is lifted toward the first aperture 108 whereby pushing also the biosignal processing device 102 toward the first aperture 108.

Figure 9:
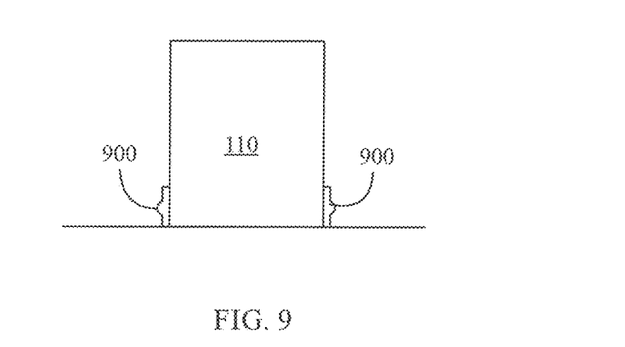
FIG. 9 illustrates an example of a seal round the electrically conductive contact structure.

In an embodiment an example of which is shown in FIG. 9, there may be a seal 900 around the electrically conductive contact structure 110. Although the electrically conductive contact structure 110 is a male connector in FIG. 9, a similar sealing may be applied to a female connector. When the counterpart 116 is in contact with the electrically conductive contact structure 110, the coupling may be dust-proof and/or water-proof. The seal 900 may also increase the friction between the polymer holder 100 and the biosignal processing device 102.

An electrode system may comprises the polymer holder 100, the electrically conductive contact structure 110, the electrodes 112, and the biosignal processing device 102 which have already been disclosed above.

Figure 10:
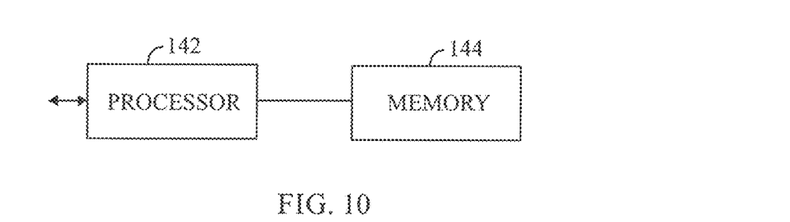
FIG. 10 illustrates an example where the biosignal processing device has at least one processor and at least one memory.

In an embodiment an example of which is shown in FIG. 10, the biosignal processing device 102 may comprise one or more processors 142, and one or more memories 144 that may include a computer program code. The one or more memories 144 and the computer program code may, with the one or more processors 142, cause the electrode system at least to process the biosignal received from the human or animal.

Figure 11:
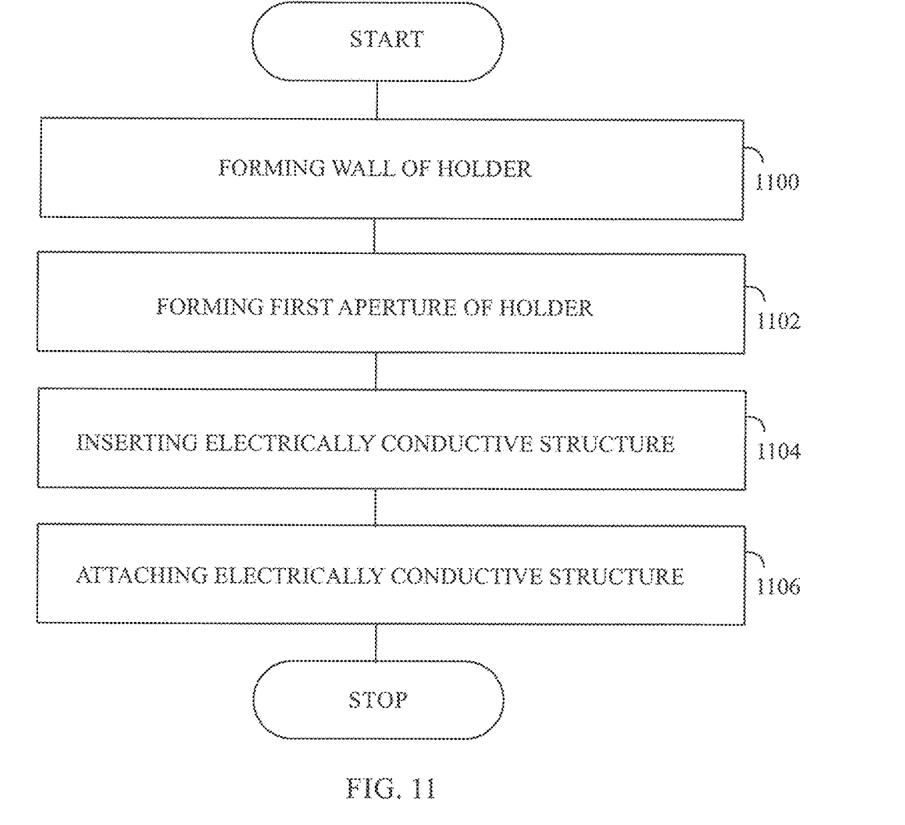
FIG. 11 illustrates an example of a flow chart of a manufacturing method.

FIG. 11 illustrates an example of a flow chart of a manufacturing method of a polymer holder 100. In step 1100, a wall 104 of the polymer holder 100 is formed in a shape of a pocket 106 that follows an outer contour of the biosignal processing device 102. In step 1102, a first aperture 108 is formed in the polymer holder 100 for allowing an insert of the biosignal processing device 102 into the pocket 106 and a removal of the biosignal processing device 102 from the pocket 106. In step 1104, an electrically conductive contact structure 110, which is electrically wired in contact with electrodes 112 that receive the at least one biosignal, is inserted at a rear section 114 of the polymer holder 100 opposite to the first aperture 108. In step 1106, the electrically conductive contact structure 110 is attached at least partly inside the wall 104, the electrically conductive contact structure 110 being for connection with a counterpart 116 of the biosignal processing device 102 in response to an insertion of the biosignal processing device 102 in the pocket 106.

In an embodiment of the manufacturing method, the electrically conductive contact structure 110 may be molded within an elastic material.

In an embodiment of the manufacturing method, a mechanism 126 is formed at the rear section 114, the mechanism 126 being configured to cause a force, to the biosignal processing device 102, directed toward the first aperture 108 in response to pressure against the polymer holder 100 at the rear section 114.

Figure 12:
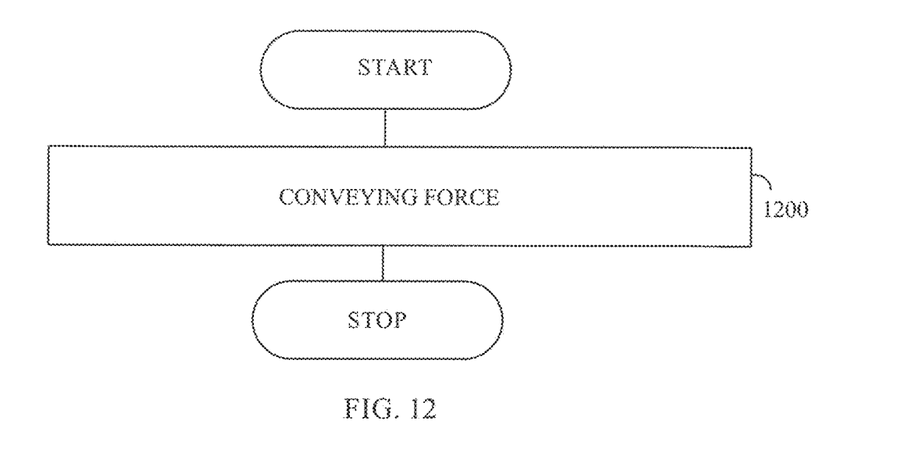
FIG. 12 illustrates of an example of a flow chart of a handling method of the polymer holder.

FIG. 12 illustrates an example of a flow chart of a handling method of a polymer holder 100. In step 1200, a force is conveyed to a biosignal processing device 102 by a mechanism 126 that is in contact with the biosignal processing device 102 at a rear section 114 of the polymer holder 100, the force moving the biosignal processing device 102 in response to a pressure against the polymer holder 102 at the rear section 114 toward a first aperture 108.

It will be obvious to a person skilled in the art that, as technology advances, the inventive concept can be implemented in various ways. The invention and its embodiments are not limited to the example embodiments described above but may vary within the scope of the claims.

The invention claimed is:

1. A polymer holder for a biosignal processing device, wherein a wall of the polymer holder is configured to form a pocket, the wall following an outer contour of the biosignal processing device, the polymer holder comprising:
   a first aperture for inserting the biosignal processing device into the pocket and removing the biosignal processing device from the pocket; and
   an electrically conductive contact structure, which is configured to be in a wired electric contact with electrodes configured to receive the at least one biosignal, at a rear section opposite to the first aperture, and the electrically conductive contact structure is at least partly attached inside the wall, the electrically conductive contact structure being configured to electrically connect with a counterpart of the biosignal processing device in response to an insert of the biosignal processing device in the pocket, the wall of the polymer holder being reshapable, the wall of the polymer holder configured to droop in response to pressure against the polymer holder at the rear section, the polymer holder comprising a mechanism configured to redirect force of the pressure to a force toward the first aperture in order to move the biosignal processing device theretoward for removal of the biosignal processing device from the pocket, the mechanism comprising a piston and at least one lever, the piston configured to move toward and fromward the first aperture, the at least one lever hinged to the piston at one end and to the polymer holder at another end, the at least one lever being configured to move the piston toward the first aperture in response to the pressure, the piston being configured to move the biosignal processing device toward the first aperture.

2. The polymer holder of claim 1, wherein the electrically conductive contact structure comprises a male connector partly inside the pocket, and the male connector being configured to connect with a female connector of the biosignal processing device in response to the insert of the biosignal processing device in the pocket.

3. The polymer holder of claim 1, wherein the electrically conductive contact structure comprises a female connector, and the female connector is configured to connect with a male connector of the biosignal processing device in response to the insert of the biosignal processing device in the pocket.

4. The polymer holder of claim 1, wherein the electrically conductive contact structure is partly within a cover of an elastic material.

5. The polymer holder of claim 1, wherein the polymer holder has a second aperture at the rear section, a normal of the second aperture being directed toward a direction perpendicular to a normal of the first aperture, the electrically conductive contact structure being inserted through the second aperture into the polymer holder.

6. The polymer holder of claim 1, wherein the polymer holder comprises a first polymer part, a second polymer part and a flexible polymer hinge, which are of the same material combined together in a common injection molding process.

7. The polymer holder of claim 1, wherein the mechanism is configured to cause the force to the biosignal processing devise directed toward the first aperture in response to pressure against the polymer holder at the rear section.

8. The polymer holder of claim 1, wherein the polymer holder comprises a first polymer part and a second polymer part, the first polymer part comprising a rail extending longitudinally in a direction from the rear section to the first aperture, the second polymer part comprising a slit into which the rail is matched for guiding the movement of the piston toward the first aperture.

9. The polymer holder of claim 7, wherein the electrically conductive contact structure comprises a cover of elastic material at the rear section, and the pressure causes the cover to reshape, push against and move the biosignal processing device toward the first aperture.

10. An electrode system, the electrode system comprising:
a polymer holder;
an electrically conductive contact structure;
electrodes; and
a biosignal processing device, a wall of the polymer holder being configured to form a pocket, the wall following an outer contour of the biosignal processing device, the polymer holder comprising a first aperture for inserting the biosignal processing device into the pocket and removing the biosignal processing device from the pocket, the polymer holder including the electrically conductive contact structure, which is configured to be in a wired electric contact with the electrodes configured to receive the at least one biosignal, at a rear section opposite to the first aperture, the electrically conductive contact structure being at least partly attached inside the wall, the electrically conductive contact structure being configured to connect with a counterpart of the biosignal processing device in response to an insert of the biosignal processing device in the pocket, the wall of the polymer holder being reshapable, the wall of the polymer holder configured to droop in response to pressure against the polymer holder at the rear section, the polymer holder comprising a mechanism configured to redirect force of the pressure to a force toward the first aperture in order to move the biosignal processing device theretoward for removal of the biosignal processing device from the pocket, the mechanism comprising a piston and at least one lever, the piston configured to move toward and fromward the first aperture, the at least one lever hinged to the piston at one end and to the polymer holder at another end, the at least one lever being configured to move the piston toward the first aperture in response to the pressure, the piston being configured to move the biosignal processing device toward the first aperture.

11. The electrode system of claim 10, wherein the biosignal processing device comprises:
one or more processors; and
one or more memories including computer program code, the one or more memories and the computer program code configured to, with the one or more processors, cause the electrode system at least to process the biosignal received from the human or animal.

12. A handling method of a polymer holder, the method comprising:
conveying, by a mechanism in contact with the biosignal processing device at a rear section of the polymer holder, a force that moves the biosignal processing devise in response to pressure of the polymer holder at the rear section toward a first aperture, wherein a wall of the polymer holder is configured to form a pocket, the wall following an outer contour of the biosignal processing device, the polymer holder having the first aperture for inserting the biosignal processing device into the pocket and removing the biosignal processing device from the pocket, the polymer holder including the electrically conductive contact structure, which is configured to be in a wired electric contact with electrodes configured to receive the at least one biosignal, at the rear section opposite to the first aperture, the electrically conductive contact structure being at least partly attached inside the wall, the electrically conductive contact structure being configured to connect with a counterpart of the biosignal processing device in response to an insert of the biosignal processing device in the pocket, the wall of the polymer holder being reshapable, the wall of the polymer holder configured to droop in response to pressure against the polymer holder at the rear section, the polymer holder comprising a mechanism configured to redirect force of the pressure to a force toward the first aperture in order to move the biosignal processing device theretoward for removal of the biosignal processing device from the pocket, the mechanism comprising a piston and at least one lever, the piston configured to move toward and fromward the first aperture, the at least one lever hinged to the piston at one end and to the polymer holder at another end, the at least one lever being configured to move the piston toward the first aperture in response to the pressure, the piston being configured to move the biosignal processing device toward the first aperture.

* * * * *